United States Patent [19]

Kopolow

[11] Patent Number: 5,219,559
[45] Date of Patent: Jun. 15, 1993

[54] COPOLYMER OF VINYL PYRROLIDONE AND A C30 ALPHA-OLEFIN IN FLAKE OR POWDER FORM, PROCESS FOR MAKING SAME, AND PERSONAL CARE COMPOSITIONS THEREWITH

[75] Inventor: Stephen L. Kopolow, Plainsboro, N.J.

[73] Assignee: ISP Investments Inc., Wilmington, Del.

[21] Appl. No.: 911,640

[22] Filed: Jul. 10, 1992

Related U.S. Application Data

[62] Division of Ser. No. 749,755, Aug. 26, 1991, Pat. No. 5,171,807.

[51] Int. Cl.$^5$ .................... A61K 7/021; A61K 7/025; A61K 7/42; A61K 7/44

[52] U.S. Cl. .................... 424/59; 424/60; 424/63; 424/64

[58] Field of Search .................... 424/59, 60, 63, 64

[56] References Cited

U.S. PATENT DOCUMENTS 4,919,934  4/1990  Deckner et al. .................... 514/873
5,026,540  6/1991  Dixon et al. .................... 424/60

*Primary Examiner*—Dale R. Ore
*Attorney, Agent, or Firm*—Walter Katz; Marilyn J. Maue; Joshua J. Ward

[57] ABSTRACT

Ganex ® copolymers in the physical form of flakes or powders is provided herein by a novel process, and used in a personal care composition.

5 Claims, No Drawings

ID FLAKE OR POWDER
COPOLYMER OF VINYL PYRROLIDONE AND A C30 ALPHA-OLEFIN IN FLAKE OR POWDER FORM, PROCESS FOR MAKING SAME, AND PERSONAL CARE COMPOSITIONS THEREWITH

This is a division of application Ser. No. 749,755, filed Aug. 26, 1991, now U.S. Pat. No. 5,171.807.

BACKGROUND OF THE INVENTION

1. This invention relates to linear copolymers of vinyl pyrrolidone and long chain alpha-olefins and, more particularly, to such copolymers in the form of flakes or powders.

2. Description of the Prior Art

U.S. Pat. Nos. 3,406,238; 3,417,054; 3,309,365; 3,423,381; and 3,423,367 describe the preparation of alkylated polymers of heterocyclic N-vinyl monomers by the simultaneous polymerization and alkylation of heterocyclic N-vinyl monomers and long chain alpha-olefin comonomers. Alkylated vinyl pyrrolidone copolymers, for example, are known as Ganex ® polymers, and are sold by International Specialty Products. Typically, Ganex ® V-216 is sold in the form of a straw-colored viscous liquid while Ganex ® V-220 is a waxy solid. Other Ganex ®polymers having different long chain alkyl groups therein are known but these are also prepared as bulk solids.

The use of Ganex ® copolymers as a waterproofing agent in sunscreen products is well known. However, its main disadvantage of bulk solids is that it is inconvenient to process into such formulations.

Accordingly, it is desired to provide such copolymers as flakes or powders which could be handled more easily, and, perhaps, have superior waterproofing properties in a personal care composition, such as a sunscreen composition than the bulk form.

Another sought-after objective of this invention is to provide a process for making copolymers of vinyl pyrrolidone and long chain alpha-olefins in the physical form of flakes or powders.

These and other objects and features of the invention will be made apparent from the following description of the invention.

SUMMARY OF THE INVENTION

What is provided herein is a process for making copolymers of vinyl pyrrolidone and long chain alpha-olefins in flake or powder form which is characterized by:

(a) olefinic fraction, containing predominately $C_{30}$ alpha-olefin in a high boiling organic solvent in the presence of a free radical initiator at a solids level of at least about 40% by weight at a temperature sufficient for activation of the initiator, (b) removing the solvent, (c) forming the molten copolymer reaction product into sheets, and (d) comminuting the sheets into flakes or powders, the melting point of the product being at least about 50° C.

In the preferred form of the invention, the organic solvent is butanol or hexanol, the melting point of the copolymer is at least 60° C., the copolymer comprises about 20% by weight of vinyl pyrrolidone and 80% by weight of a $C_{30}$ alpha-olefin, and residual olefin is substantially absent from the copolymer.

DETAILED DESCRIPTION OF THE INVENTION

In accordance with the invention, a mixture of vinyl pyrrolidone and a long chain alpha-olefin, such as a linear $C_{30}$ alpha-olefin fraction, is provided in a high boiling organic solvent, such as butanol or hexanol, at a solids level of at least about 40% by weight, preferably 50% or more. The mixture is copolymerized in the presence of about 5-15% by weight of a free radical initiator based on vinyl pyrrolidone at a temperature sufficient for activation of the initiator, usually about 130°-35° C. The solvent is then removed from the reaction product by stripping off the solvent, forming the resultant molten copolymer into sheets, and comminuting the sheets into flakes or powders. The melting point of the resultant copolymer sheets is at least 50° C., preferably at least 60° C.

The invention will now be described by reference to the following working examples.

EXAMPLE 1

A glass kettle fitted with a nitrogen inlet, a thermometer, a condenser and an anchor agitator was charged with hexanol solvent and a predominately $C_{30}$ alpha-olefin fraction ("Gulfene $C_{30+}$" sold by Chevron Olefins Division, Houston, Tex.) monomer. The mixture was heated to 80° C. to dissolve the olefin and then stabilized vinyl pyrrolidone monomer and 12 g. of t-butyl peroxide initiator were added. The solids level of the solution was 51%. The reaction solution then was heated to 130°-140° C. and held at that temperature for 20-24 hours. The reaction product was cooled to 80° C., and the solvent was removed under vacuum. The molten residue then was cooled into sheets. The resultant copolymer, which had a melting point of 63°-64° C., was commingled into flakes and powders. The bromine number of the product was 1-10, which indicated that the residual alpha-olefin level was quite low.

EXAMPLE 2

The procedure of Example 1 was followed using butanol solvent with similar results.

EXAMPLE 3

The materials of Example 1 and 2 were used in a conventional sunscreen composition containing the copolymer of Examples 1 and 2. The composition exhibited superior waterproofing properties versus the same composition containing similar amounts of Ganex ® V-220 (ISP) which exists in bulk form as a waxy solid.

What is claimed is:

1. A personal care composition having improved waterproofing properties and high temperate stability comprising (a) an active personal care material and (b) a copolymer or vinyl pyrrolidone and an olefinic fraction containing predominantly a $C_{30}$ alpha-olefin provided in flake or powder form having a melting point of at least 50° C.

2. A personal care composition according to claim 1 where (a) is a sunscreen, an eye shadow or a lip balm.

3. A personal care composition according to claim 1 wherein said melting point is at least 60° C., and the copolymer comprises about 20% by weight vinyl pyrrolidone and about 80% by weight of said $C_{30}$ alpha-olefin.

4. A personal care composition according to claim 1 wherein said copolymer comprises about 1-10% by weight of the composition.

5. A sunscreen composition according to claim 1 the material comprising (a) an active sunscreen material, and (b) about 1-10% by weight of a copolymer of vinyl pyrrolidone and an olefinic fraction containing predominately a $C_{30}$ alpha-olefin having a melting point of at least 50° C.

* * * * *